United States Patent [19]

Wright et al.

[11] Patent Number: 4,996,378

[45] Date of Patent: Feb. 26, 1991

[54] PROCESS FOR PRODUCTION OF 1,1-DICHLORO-1-FLUOROETHANE AND/OR 1-CHLORO-1,1-DIFLUOROETHANE

[75] Inventors: Danny W. Wright, Hickory; Barry L. Wagner, Benton, both of Ky.

[73] Assignee: Atochem North America, Inc., Philadelphia, Pa.

[21] Appl. No.: 379,518

[22] Filed: Jul. 13, 1989

[51] Int. Cl.$^5$ .............................................. C77C 17/20
[52] U.S. Cl. ................................................... 570/164
[58] Field of Search ......................................... 570/164

[56] References Cited

U.S. PATENT DOCUMENTS 3,833,676  9/1974  Ukaji et al. ........................... 570/164

*Primary Examiner*—Alan Siegel
*Attorney, Agent, or Firm*—Seidel, Gonda, Lavorgna & Monaco

[57] ABSTRACT

1,1-Dichloro-1-fluoroethane and/or 1-chloro-1,1-difluoroethane are selectively produced by fluorination of 1,1,1-trichloroethane. Conditions in a first reaction zone selected to preferentially form 1,1-dichloro-1-fluoroethane. The reaction effluent is split between a 1,1-dichloro-1-fluoroethane recovery system, and a second reaction zone. The effluent from the latter is routed to 1-chloro-1,1,-difluoroethane recovery system. The second reaction zone conditions are selected for form 1-chloro-1,1-difluoroethane. The ratio of product formed by the overall process may be varied from up to 98% 1,1-dichloro-1-fluoroethane to greater than 98% 1-chloro-1,1-difluoroethane.

13 Claims, 1 Drawing Sheet

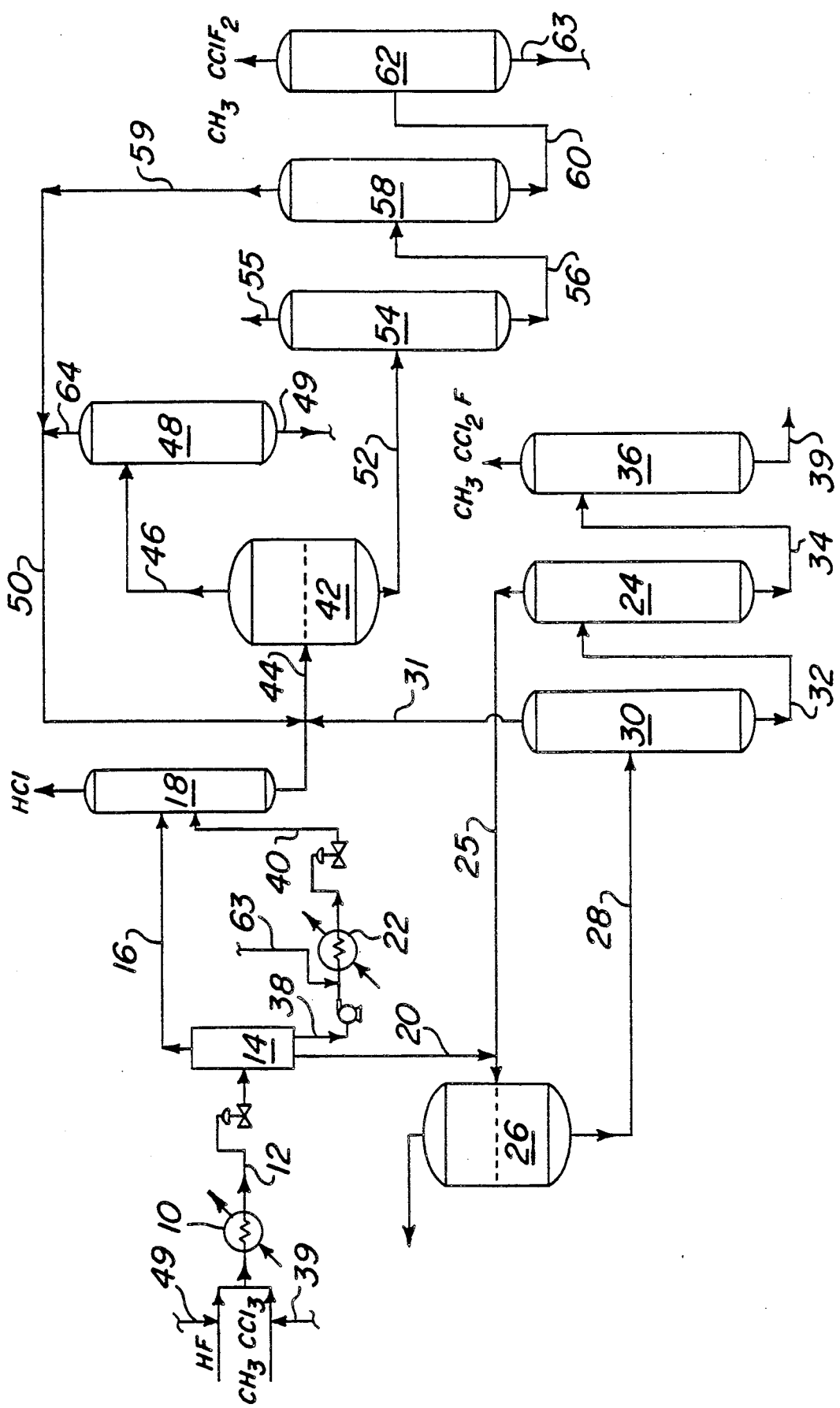

PROCESS FOR PRODUCTION OF 1,1-DICHLORO-1-FLUOROETHANE AND/OR 1-CHLORO-1,1-DIFLUOROETHANE

FIELD OF THE INVENTION

The invention relates generally to the production of 1,1-dichloro-1-fluoroethane and/or 1-chloro-1,1-difluoroethane, and more particularly to a process for the production of 1,1-dichloro-1-fluoroethane and/or 1-chloro-1,1-difluoroethane by the fluorination of 1,1,1-trichloroethane with hydrogen fluoride.

BACKGROUND OF THE INVENTION 1,1-Dichloro-1-fluoroethane (hereinafter referred to by its American Society of Refrigeration Engineers designation, "141b") is presently under consideration as a replacement for trichlorofluoromethane as a foam blowing agent. It has a substantially lower ozone depletion index than trichlorofluoromethane. Moreover, 141b displays a 10-15% greater blowing efficiency in rigid foam, and an improved solubility in aromatic polyester polyol, in comparison to trichlorofluoromethane.

1-Chloro-1,1-difluoroethane (hereinafter "142b") is the starting material for the production of polyvinylidene fluoride.

The fluorination of 1,1,1-trichloroethane (hereinafter "140a") to manufacture 142b results in a product stream which includes unreacted starting materials as well as by-products including HCl, vinylidene chloride and 1,1,1-trifluoroethane (hereinafter "143a"). The reactor bottoms include unreacted hydrogen fluoride, pentafluorobutane and possibly small amounts of other organics. Pentafluorobutane is the principal component of reactor tars which accumulate in the reactor bottoms. Vinylidene chloride and pentafluorobutane have boiling points so close to 141b that they cannot be removed by simple distillation. Additional steps for separating 141b from these undesired side products are required, contributing to the overall expense of the process. Moreover, large yield losses are suffered when reactor tars are dumped.

U.S. Pat. No. 3,833,676 discloses a non-catalytic process for the fluorination of 140a with hydrogen fluoride to produce 141b and 142b, without formation of tar substances.

SUMMARY OF THE INVENTION

A process for the production of 141b and/or 142b is provided. 1,1,1-Trichloroethane is treated in a first reaction zone with HF to selectively form 141b. The effluent from the first reaction zone is divided to form first and second 141b-containing streams. The first 141b-containing stream is cooled to separate the stream into a hydrogen fluoride-rich liquid phase and a 141b-rich liquid phase. The two phases are separated. The second 141b-containing stream is treated with hydrogen fluoride in a second reaction zone to form 142b. The second reaction zone effluent is cooled to separate the effluent into a hydrogen fluoride-rich liquid phase and a 142b-rich liquid phase. The phases are separated.

Production of 141b and 142b is thus carried out in two separate reactors in order to control the ultimate yield structure, and to allow the separate reactions to proceed under the mildest possible conditions. This greatly minimizes the formation of undesirable side products. The reaction mixtures are processed via distillation and phase separation to recover the desired products 141b and 142b.

As used in the herein specification and appended claims the expression "selectively form" with respect to a desired chemical species means generating a product which comprises at least 50% by weight the desired species.

DESCRIPTION OF THE FIGURE

The FIGURE is a schematic illustration an embodiment of the process of the invention.

DETAILED DESCRIPTION OF THE INVENTION

According to the present invention, the fluorination of 140a in the first reaction zone is conducted in a manner such that 141b is selectively formed over 142b. This is accomplished using relatively mild reaction conditions and relatively brief reactant resident times in the reaction zone. Accordingly, 140a is preferably treated in the first reaction zone with hydrogen fluoride in a molar ratio of hydrogen fluoride to 1,1,1-trichloroethane of at least about 20:1, at a temperature of from about 80° C. to about 95° C., for a period of time from about 0.5 minutes to about 2 minutes.

The effluent from the first reaction zone, comprising primarily 141b and unreacted 140a and hydrogen fluoride, is divided into two streams. The one stream is diverted for removal of 141b by phase separation and distillation. The second stream is fed to a second reaction zone for continued fluorination under conditions favoring formation of the more fluorinated product, 142b. This second stream is preferably treated in the second reaction zone with hydrogen fluoride in a molar ratio of hydrogen fluoride to 141b (based on the amount of 141b in the stream) of at least about 20:1, at a temperature of from about 95° C. to about 110° C., for from about 5 minutes to about 10 minutes. 1-Chloro-1,1-difluoroethane is subsequently recovered from the second reaction zone reaction mixture by phase separation and distillation.

The reaction conditions in the first reaction zone, as described above, yield a conversion of 140a to 141b from about 80% to about 90%. The total conversion to 141b and 142b in the first reaction zone ranges from 82 to 97%.

The first and second reaction zones may comprise any form of reactor known to those skilled in the art useful for conducting fluorination of chlorohydrocarbons. The reactions may be catalyzed, but are preferably not catalyzed. Preferably, both reaction zones comprise plug flow reactors. According to the principles of plug flow, also known as piston flow, the fluid comprising the reactor feed passes through the reaction zone with a substantially uniform velocity profile such that there is no mixing of elements of the reactor feed which have entered the reactor at different times. Thus, all fluid in the reactor remains in the reaction zone for substantially the same amount of time. Accordingly, greater control over reaction conditions, and a uniformity of product, is achieved.

We have found that a molar ratio of hydrogen fluoride to 140a of at least about 20:1, preferably atleast about 25:1, is generally required to ensure that the fluorination reaction proceeds with the desired velocity. The fluorination of 140a to 141b is very rapid at HF to 140a molar ratios of at least 20:1, and particularly at ratios of at least 25:1. At a ratio of only 4:1 hydrogen fluoride to 140a, a scant 8.2 mole % conversion of 140a is achieved with a residence time as long as 15 minutes. Thus, hydrogen fluoride is preferably present in a sufficient molar excess with respect to 140a in the reaction mixture to reach the solubility limits of 140a in hydrogen fluoride. Once mutual solubility is achieved, the reaction proceeds very rapidly. Residence time and temperature then become contributing factors to the overall conversion of 140a to fluorinated product. We have found that at low hydrogen fluoride levels, the residence time and temperature have no significant affect on the overall conversion of 140a to fluorinated product.

While it may be possible to increase the reaction temperature to increase the solubility of 140a in hydrogen fluoride, and therefore reduce the amount of hydrogen fluoride required in the reaction mixture, such higher reaction temperatures are undesirable, since they appear to lead to the formation of undesirable side products, and require exotic metallurgy for reactor hardware. By carrying out the respective fluorination reactions in the first and second reaction zones, under the relatively mild conditions specified herein, reactor vessels of conventional fabrication may be advantageously employed.

The operating pressures in the reactors comprising the reaction zones are selected so as to maintain the reactor contents in the liquid phase. Thus, the operating pressure is preferably at least about 15.5 kg/cm$^2$ in the first reaction zone, and somewhat higher in the second reaction zone. Reactor performance for both reactions is generally independent of pressure, so long as the pressure is high enough to assure liquid phase operation in each reactor.

Due to the short residence times and mild reaction conditions employed in the practice of the present invention, side products such as vinylidene chloride and pentafluorobutane are not formed. Both of these compounds have boiling points so close to that of the desired product 141b that they cannot be removed from the 141b product stream by simple distillation. The practice of the present invention therefore avoids the additional steps for removal of these compounds. Moreover, the present invention avoids the formation of heavy organics in the reaction mixture, thereby eliminating the large yield losses suffered in dumping tar build-up from the fluorination reactor. Moreover, the process of the present invention allows the ratio of 141b to 142b product to be varied from up to 98% 141b to greater than 98% 142b, by the simple expedient of diverting more or less product from the 141b recovery portion of the system to the second reaction zone, wherein 141b is converted to 142b.

The process of the invention is illustrated in greater detail in the FIGURE. Hydrogen fluoride and 140a from supply tanks (not shown) are pumped to reactor 10, which is preferably a plug flow reactor, wherein a portion of the 140a is converted to 141b. The conditions in the reactor are selected such that 141b is formed preferentially over the more fluorinated product 142b. The effluent from the reactor provides a product stream in line 12 at a temperature of, for example, 88° C., containing 141b and unreacted hydrogen fluoride and 140a, in addition to HCl. The product stream is fed to a flash drum 14 wherein the bulk of the HCl from the reaction is removed and shunted through line 16 to HCl stripper column 18. Column 18 may be operated at, for example, a bottom temperature of about 82° C., and a pressure of about 7.4 kg/cm$^2$. The inlet temperature and drum pressure of flash drum 14 are determined by the HCl stripper column pressure. The liquid from the flash drum, constituting the product stream from reactor 10 from which a substantial portion of the HCl has been removed, is split between a 141b recovery system via line 20 and a second reactor 22 via line 38 wherein 141b and any unreacted 140a are converted to 142b.

Tracing the 141b recovery portion of the system, the 141b-containing stream carried through line 20 is combined with an azeotropic mixture of 141b and HF recycled from a downstream distillation column 24 which shall be described later. The combined stream is fed to a phase separator 26. In the phase separator, which is operated at, for example, a temperature of about 0° C., and atmospheric pressure, the feed stream rapidly separates into an HF-rich upper phase and a 141b-rich lower phase. The HF-rich phase contains, by weight, about 95% HF and about 5% 141b. This material is recycled to the hydrogen fluoride feed for reactor 10. The 141b-rich phase from separator 26 contains, by weight, about 99% 141b and about 1% HF and trace amounts of 142b, 143b and possibly HCl. This 141b-rich stream is pumped through line 28 to light ends column 30, which is operated, for example, at about 2.8 kg/cm and about 77° C. at the top. The overhead stream from light ends column 30 is recycled via line 31 to the feed of a phase separator 42, described in more detail below. The column 30 overhead stream contains hydrogen fluoride, HCl, 142b and 143a. The bottoms from light ends column 30 is fed through line 32 to azeotrope column 24. The latter is operated, for example, at 1.4 kg/cm$^2$ and a bottom temperature of about 60° C. The 141b/HF azeotrope (comprising about 66% 141b and about 34% HF) is recycled through line 25 back to phase separator 26, after combination with the product stream 20 from flash drum 14. The essentially HF-free bottoms stream in line 34 leading from azeotrope column 24 is fed to column 36 for further purification. Column 36 is operated, for example, at a pressure of about 0.7 kg/cm$^2$ and a bottom temperature of about 92° C. The overhead of column 36 comprises essentially pure 141b. The bottoms from column 36 contains unreacted 140a which is recycled via line 39 to reactor 10.

Turning to the 142b-producing cycle of the system, the stream in line 38 from flash drum 14 is fed to reactor 22, which is preferably a plug flow reactor. The reaction conditions are selected such that 141b, and any unreacted 140a, in the stream are converted to 142b. This provides a product stream comprising 142b, hydrogen fluoride, HCl and possibly 143a, at a temperature of, for example, 104° C. The reaction products are fed through line 40 to HCl stripper column 18. The product stream from the stripper is combined with the overhead from light ends column 30 (supplied via line 31) and routed through line 44 to phase separator 42.

Phase separator 42 is similar in construction to phase separator 26. Phase separator 42 is operated at a temperature of, for example, about −20° C. and at a pressure of, for example, about 0.01 kg/cm$^2$. The feed stream rapidly separates into a HF-rich upper phase and a 142b-rich lower phase. The HF-rich upper phase, which contains, e.g., by weight 60% HF and 40% 142b, is fed through line 46 to azeotrope column 48. Azeotrope column 48 is operated, for example, at a bottom temperature of about 54° C. and a pressure of about 2.1 kg/cm$^2$. The composition of the azeotrope overhead stream is, by weight, about 88% 142b and 12% HF. The overhead stream is recycled to the feed 44 of phase separator 42 through line 50. The essentially 142b-free bottoms stream from column 48 is recycled via line 49 to the hydrogen fluoride feed of reactor 10.

The 142b-rich phase from phase separator 42, which contains about 97% 142b, 3% hydrogen fluoride, and possibly trace amounts of 143a and HCl, is pumped through line 52 to light ends column 54. Light ends column 54 is similar to light ends column 30 in construction and operation. It is operated at, for example, about 8.4 kg/cm$^2$ and a bottom temperature of about 57° C. An overhead stream comprising HCl and 143a is removed via line 55 and routed to a waste incinerator (not shown). The bottom product from column 54 is fed by line 56 to azeotrope column 58, which is operated, for example, at a pressure of about 3.5 kg/cm$^2$, and at a temperature of about 35° C. at the bottom. The essentially HF-free bottoms stream in line 60 is removed for further purification in column 62. Column 62 is operated, for example, at a pressure of about 4.9 kg/cm$^2$ and a bottom temperature of about 83° C. The 142b/HF azeotrope is removed at the overhead of column 58, combined via line 59 with the overhead in line 64 from azeotrope column 48, and recycled back to the feed of phase separator 42. The bottoms from column 62, which comprises any unreacted 140a or 141b, is recycled via line 63 back to reactor 22 or incinerated. Essentially pure 142b is obtained as the overhead from column 62.

The conditions and proportions in the foregoing description are for illustration only and should not be construed as limiting the scope of the invention.

The present invention may be embodied in other specific forms without departing from the spirit or essential attributes thereof and, accordingly, reference should be made to the appended claims, rather than to the foregoing specification, as indicating the scope of the invention.

We claim:
1. A process for the production of 1,1-dichloro-1-fluoroethane and/or 1-chloro-1,1-difluoroethane comprising:
    (a) treating 1,1,1-trichloroethane in a first reaction zone with hydrogen fluoride in a molar ratio of hydrogen fluoride to 1,1,1-trichloroethane of at least about 20:1 for a period of time to selectively form 1,1-dichloro-1-fluoroethane over 1-chloro-1,1-difluoroethane;
    (b) forming first and second 1,1-dichloro-1-fluoroethane-containing streams from the first reaction zone effluent;
    (c) cooling the first 1,1-dichloro-1-fluoroethane-containing stream to separate said stream into a hydrogen fluoride-rich liquid phase and a 1,1-dichloro-1-fluoroethane-rich liquid phase, and separating the two phases;
    (d) treating the second 1,1-dichloro-1-fluoroethane-containing stream with hydrogen fluoride in a second reaction zone in a molar ratio of at least about 20:1 of hydrogen fluoride to 1,1-dichloro-1-fluoroethane in the second 1,1-dichloro-1-fluoroethane-containing stream for a period of time sufficient to form 1-chloro-1,1-difluoroethane; and
    (e) cooling the effluent from the second reaction zone to separate said effluent into a hydrogen fluoride-rich liquid phase and a 1-chloro-1,1-difluoroethane-rich liquid phase, and separating the two phases.

2. A process according to claim 1 wherein step (a) comprises selectively forming 1,1-dichloro-1-fluoroethane by treating 1,1,1-trichloroethane in a first reaction zone with hydrogen fluoride at a treatment temperature of from about 80° C. to about 95° C., for a period of time from about 0.5 minutes to about 2 minutes.

3. A process according to claim 2 wherein step (d) comprises forming 1-chloro-1,1-difluoroethane by treating the second 1,1-dichloro-1-fluoroethane-containing stream with hydrogen fluoride at a treatment temperature of from about 95° C. to about 110° C., for from about 5 minutes to about 10 minutes.

4. A process according to claim 1 wherein the first and second reaction zones comprise plug flow reactors.

5. A process according to claim 1 including removing HCl from the first reaction zone effluent.

6. A process according to claim 1 including distilling an azeotropic mixture of hydrogen fluoride and 1-chloro-1,1-difluoroethane from the 1-chloro-1,1-difluoroethane-rich and hydrogen fluoride-rich liquid phases in (e) and combining the azeotropic mixtures with the effluent from the second reaction zone.

7. A process according to claim 6 including returning the hydrogen fluoride from the distillation of the hydrogen fluoride-rich liquid phase to the first reaction zone.

8. A process according to claim 1 including distilling an azeotropic mixture of hydrogen fluoride and 1,1-dichloro-1-fluoroethane from the 1,1-dichloro-1-fluoroethane-rich liquid phase from (c) and combining the azeotropic mixture with the first reaction zone effluent.

9. A process according to claim 8 including returning the hydrogen fluoride-rich liquid phase from (c) to the first reaction zone.

10. A process, for the production of 1,1-dichloro-1-fluoroethane and/or 1-chloro-1,1-difluoroethane comprising:
    (a) selectively forming 1,1-dichloro-1-fluoroethane by treating 1,1,1-trichloroethane in a first reaction zone with hydrogen fluoride in a molar ratio of hydrogen fluoride to 1,1,1-trichloroethane of at least about 20:1 at a temperature of from about 80° C. to about 95° C., for a period of time from about 0.5 minutes to about 2 minutes;
    (b) forming first and second 1,1-dichloro-1-fluoroethane-containing streams from the first reaction zone effluent;
    (c) recovering 1,1-dichloro-1-fluoroethane from the first 1,1-dichloro-1-fluoroethane-containing stream; and
    (d) forming 1-chloro-1,1-difluoroethane in a second reaction zone by treating the second 1,1-dichloro-1-fluoroethane-containing stream with hydrogen fluoride in molar ratio of at least about 20:1 with respect to 1,1-dichloro-1-fluoroethane in said second 1,1-dichloro-1-fluoroethane-containing stream, at a temperature of from about 95° C. to about 110° C., for from about 5 minutes to about 10 minutes.

11. A process according to claim 10 wherein the step of recovering 1,1-dichloro-1-fluoroethane comprises cooling the first 1,1-dichloro-1-fluoroethane-containing stream to separate said stream into a hydrogen fluoride-rich liquid phase and a 1,1-dichloro-1-fluoroethane-rich liquid phase, and separating the two phases.

12. A process according to claim 11 wherein the effluent from the second reaction zone is cooled to separate said effluent into a hydrogen fluoride-rich liquid phase and a 1-chloro-1,1-difluoroethane-rich liquid phase, and separating the two phases.

13. A process according to claim 12 wherein the first and second reaction zones comprise plug flow reactors.

* * * * *

UNITED STATES PATENT AND TRADEMARK OFFICE
CERTIFICATE OF CORRECTION

PATENT NO. : 4,996,378

DATED : February 26, 1991

INVENTOR(S) : Danny W. Wright, et al.

It is certified that error appears in the above—identified patent and that said Letters Patent is hereby corrected as shown below:

Claim 6, Column 6, line 13, add --1-- after "claim"; in the

Title Page:
Abstract, line 9, change "for" to --to--.

Signed and Sealed this

Twenty-eighth Day of July, 1992

Attest:

DOUGLAS B. COMER

Attesting Officer     Acting Commissioner of Patents and Trademarks